(12) United States Patent
Nakatsuji

(10) Patent No.: US 10,617,389 B2
(45) Date of Patent: Apr. 14, 2020

(54) ULTRASOUND OBSERVATION APPARATUS, METHOD OF OPERATING ULTRASOUND OBSERVATION APPARATUS, AND COMPUTER-READABLE RECORDING MEDIUM

(71) Applicant: OLYMPUS CORPORATION, Tokyo (JP)

(72) Inventor: Tomohiro Nakatsuji, Akishima (JP)

(73) Assignee: OLYMPUS CORPORATION, Tokyo (JP)

(*) Notice: Subject to any disclaimer, the term of this patent is extended or adjusted under 35 U.S.C. 154(b) by 406 days.

(21) Appl. No.: 15/723,385

(22) Filed: Oct. 3, 2017

(65) Prior Publication Data
US 2018/0035978 A1 Feb. 8, 2018

Related U.S. Application Data

(63) Continuation of application No. PCT/JP2016/080607, filed on Oct. 14, 2016.

(30) Foreign Application Priority Data

Oct. 23, 2015 (JP) ................. 2015-208648

(51) Int. Cl.
*A61B 8/00* (2006.01)
*A61B 8/08* (2006.01)
(Continued)

(52) U.S. Cl.
CPC ............. *A61B 8/461* (2013.01); *A61B 8/08* (2013.01); *A61B 8/12* (2013.01); *A61B 8/48* (2013.01);
(Continued)

(58) Field of Classification Search
CPC .. A61B 8/461; A61B 8/08; A61B 8/12; A61B 8/48
See application file for complete search history.

(56) References Cited

U.S. PATENT DOCUMENTS 6,017,309 A 1/2000 Washburn et al.
9,060,737 B2 6/2015 Matsumura et al.
(Continued)

FOREIGN PATENT DOCUMENTS

JP 4919972 B2 4/2012
JP 5079177 B2 11/2012
(Continued)

OTHER PUBLICATIONS

International Search Report dated Dec. 13, 2016 issued in PCT/JP2016/080607.
(Continued)

*Primary Examiner* — Joseph M Santos Rodriguez
(74) *Attorney, Agent, or Firm* — Scully, Scott, Murphy & Presser, P.C.

(57) ABSTRACT

An ultrasound observation apparatus includes: a feature calculation unit configured to calculate a plurality of features based on the ultrasound signal; a feature image data generation unit configured to generate feature image data in which a feature of a display target to be displayed together with the ultrasound image, among the plurality of features calculated by the feature calculation unit, are colorized with a predetermined display specification; and a display specification setting unit configured to set at least one of a colorization range of the feature of the display target and a change rate of hue of the feature of the display target, which are display specifications of the feature of the display target, by comparing a representative value of other feature other than the feature of the display target with a threshold value.

9 Claims, 13 Drawing Sheets

(51) Int. Cl.
  *G01S 7/52* (2006.01)
  *A61B 8/12* (2006.01)
  *G06F 3/0484* (2013.01)

(52) U.S. Cl.
  CPC .......... *A61B 8/5207* (2013.01); *A61B 8/5269* (2013.01); *G01S 7/52033* (2013.01); *G01S 7/52036* (2013.01); *G01S 7/52042* (2013.01); *G01S 7/52071* (2013.01); *G06F 3/04845* (2013.01); *A61B 8/485* (2013.01); *A61B 8/5246* (2013.01)

(56) References Cited

U.S. PATENT DOCUMENTS

| | | |
|---|---|---|
| 2009/0143676 A1 | 6/2009 | Matsumura |
| 2010/0036250 A1 | 2/2010 | Shin et al. |
| 2010/0220901 A1 | 9/2010 | Matsumura |
| 2013/0012818 A1 | 1/2013 | Miyaki |
| 2013/0030296 A1 | 1/2013 | Miyaki |
| 2013/0096429 A1 | 4/2013 | Noguchi |
| 2015/0080730 A1 | 3/2015 | Kanayama et al. |
| 2015/0164480 A1 | 6/2015 | Watanabe et al. |

FOREIGN PATENT DOCUMENTS

| | | |
|---|---|---|
| JP | 5160227 B2 | 3/2013 |
| WO | 94/23652 A1 | 10/1994 |
| WO | WO 2012/011414 A1 | 1/2012 |
| WO | WO 2012/063929 A1 | 5/2012 |

OTHER PUBLICATIONS

Japanese Decision to Grant a Patent, dated May 30, 2017 issued in JP 2017-516795.
Extended Supplementary European Search Report dated Jun. 26, 2019 in European Patent Application No. 16 85 7383.0.

ULTRASOUND OBSERVATION APPARATUS, METHOD OF OPERATING ULTRASOUND OBSERVATION APPARATUS, AND COMPUTER-READABLE RECORDING MEDIUM

CROSS-REFERENCE TO RELATED APPLICATIONS

This application is a continuation of PCT international application Ser. No. PCT/JP2016/080607 filed on Oct. 14, 2016 which designates the United States, incorporated herein by reference, and which claims the benefit of priority from Japanese Patent Application No. 2015-208648, filed on Oct. 23, 2015, incorporated herein by reference.

BACKGROUND

1. Technical Field

The disclosure relates to an ultrasound observation apparatus for observing a tissue of an observation target using ultrasound, a method of operating an ultrasound observation apparatus, and a computer-readable recording medium.

2. Related Art

In some cases, ultrasound is applied in order to observe characteristics of living tissues or materials of an observation target. Specifically, ultrasound is transmitted to the observation target, and predetermined signal processing is applied to ultrasound echoes reflected by the observation target, so that information on features of the observation target is obtained.

As a technique for observing tissue characterization of an observation target such as a subject by using ultrasound, a technique for imaging a feature data of a frequency spectrum of a received ultrasound signal is known (for example, refer to JP 5160227 B2). In this technique, after extracting a feature data of a frequency spectrum as a quantity representing the tissue characterization of an observation target, a feature data image to which visual information corresponding to the feature data is attached is generated and displayed. A user such as a doctor diagnoses the tissue characterization of a specimen by viewing the displayed feature data image.

For example, in JP 5160227 B2, an elastic image in which the hardness of a tissue of an observation target is imaged is displayed, and color information to which a color is given according to a feature data is displayed. The elastic image is generally called an elastography, acquires information (feature data) on the hardness of the observation target in the set region, and superimposes color information corresponding to the feature data on the ultrasound image. Specifically, JP 5160227 B2 discloses that an elastic image that is gradated on the basis of a relative ratio between a distortion at a measurement point of a measurement target and a distortion of a reference region is displayed as a reference to the distortion of the reference region selected within the image.

SUMMARY

In some embodiments, an ultrasound observation apparatus generates an ultrasound image based on an ultrasound signal acquired by an ultrasound probe, the ultrasound probe including an ultrasound transducer configured to transmit ultrasound to an observation target and receive the ultrasound reflected from the observation target. The ultrasound observation apparatus includes: a feature calculation unit configured to calculate a plurality of features based on the ultrasound signal; a feature image data generation unit configured to generate feature image data in which a feature of a display target to be displayed together with the ultrasound image, among the plurality of features calculated by the feature calculation unit, are colorized with a predetermined display specification; and a display specification setting unit configured to set at least one of a colorization range of the feature of the display target and a change rate of hue of the feature of the display target, which are display specifications of the feature of the display target, by comparing a representative value of other feature other than the feature of the display target with a threshold value.

In some embodiments, provided is a method of operating an ultrasound observation apparatus for generating an ultrasound image based on an ultrasound signal acquired by an ultrasound probe, the ultrasound including an ultrasound transducer configured to transmit ultrasound to an observation target and receive the ultrasound reflected from the observation target. The method includes: calculating, by a feature calculation unit, a plurality of features based on the ultrasound signal; setting, by comparing a representative value of other feature other than a feature of a display target to be displayed together with the ultrasound image, among the plurality of features calculated by the feature calculation unit, with a threshold value by a display specification setting unit, at least one of a colorization range of the feature of the display target and a change rate of hue of the feature of the display target, which are display specifications of the feature of the display target; and generating, by a feature image data generation unit, feature image data in which the feature of the display target is colorized with a predetermined display specification.

In some embodiments, provided is a non-transitory computer-readable recording medium with an executable program stored thereon. The program causes an ultrasound observation apparatus for generating an ultrasound image based on an ultrasound signal acquired by an ultrasound probe, the ultrasound including an ultrasound transducer configured to transmit ultrasound to an observation target and receive the ultrasound reflected from the observation target, the operation program causing the ultrasound observation apparatus to execute: calculating, by a feature calculation unit, a plurality of features based on the ultrasound signal; setting, by comparing a representative value of other feature other than a feature of a display target to be displayed together with the ultrasound image, among the plurality of features calculated by the feature calculation unit, with a threshold value by a display specification setting unit, at least one of a colorization range of the feature of the display target and a change rate of hue of the feature of the display target, which are display specifications of the feature of the display target; and generating, by a feature image data generation unit, feature image data in which the feature of the display target is colorized with a predetermined display specification.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, modes for carrying out the disclosure (hereinafter, referred to as "embodiments") will be described with reference to the accompanying drawings.

First Embodiment

Figure 1:
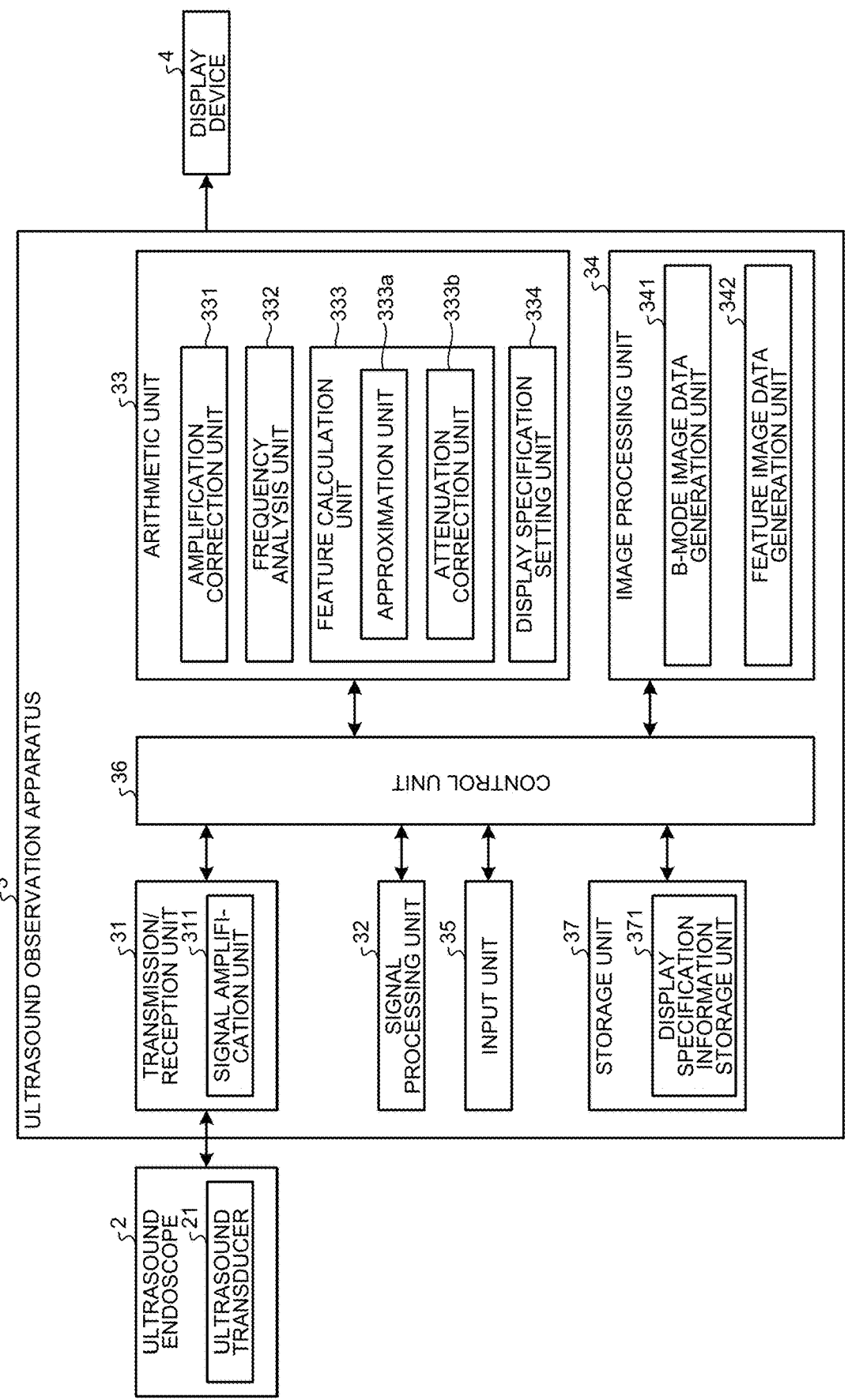
FIG. 1 is a block diagram illustrating a configuration of an ultrasound observation system including an ultrasound observation apparatus according to a first embodiment of the disclosure.

FIG. 1 is a block diagram illustrating a configuration of an ultrasound observation system 1 including an ultrasound observation apparatus 3 according to a first embodiment of the disclosure. The ultrasound observation system 1 illustrated in the figure is configured to include an ultrasound endoscope 2 (ultrasound probe) that transmits ultrasound to a subject as an observation target and receives the ultrasound reflected from the subject, the ultrasound observation apparatus 3 for generating an ultrasound image on the basis of the ultrasound signal acquired by the ultrasound endoscope 2, and a display device 4 for displaying the ultrasound image generated by the ultrasound observation apparatus 3.

The ultrasound endoscope 2 is configured to include, at the distal end portion of the ultrasound endoscope, an ultrasound transducer 21 for irradiating the subject with an ultrasound pulse (acoustic pulse) obtained by converting an electrical pulse signal received from the ultrasound observation apparatus 3 into the ultrasound pulse and converting an ultrasound echo reflected by the subject into an electrical echo signal (ultrasound signal) represented by voltage change and outputting the electrical echo signal. The ultrasound transducer 21 may be any of a convex oscillator, a linear oscillator, and a radial oscillator. In the ultrasound endoscope 2, the ultrasound transducer 21 may be allowed to mechanically scan, or a plurality of elements in the form of an array may be provided as the ultrasound transducer 21, and thus, the elements related to transmission and reception are electronically switched or transmission and reception of each element are delayed, so that the ultrasound transducer may be allowed to electronically scan.

Typically, the ultrasound endoscope 2 includes an imaging optical system and an imaging device, is inserted into a digestive tract (esophagus, stomach, duodenum, large intestine) or a respiratory organ (trachea/bronchus) of a subject and may capture the digestive tract, the respiratory organ and surrounding organs (pancreas, gallbladder, bile duct, biliary tract, lymph node, mediastinum, blood vessels, or the like). In addition, the ultrasound endoscope 2 is configured to include a light guide for guiding illumination light to be illuminated to the subject at the time of imaging. The distal end portion of the light guide reaches the distal end of the insertion portion of the ultrasound endoscope 2 to the subject, and the proximal end portion is connected to a light source device that generates the illumination light. In addition, the ultrasound endoscope is not limited to the ultrasound endoscope 2 and may be an ultrasound probe not including the imaging optical system and the imaging device.

The ultrasound observation apparatus 3 is configured to include a transmission/reception unit 31 electrically connected to the ultrasound endoscope 2 to transmit a transmission signal (pulse signal) configured with a high voltage pulse on the basis of a predetermined waveform and transmission timing to the ultrasound transducer 21 and to receive an echo signal as an electrical reception signal from the ultrasound transducer 21 to generate and output data of a digital high frequency (RF: Radio Frequency) signal (hereinafter, referred to as RF data), a signal processing unit 32 for generating digital B-mode reception data on the basis of the RF data received from the transmission/reception unit 31, an arithmetic unit 33 for performing predetermined arithmetic operation on the RF data received from the transmission/reception unit 31, an image processing unit 34 that generates various image data, an input unit 35 that is realized by using a user interface such as a keyboard, a mouse, a touch panel, or the like and receives input of various types of information, a control unit 36 for controlling the entire ultrasound observation system 1, and a storage unit 37 that stores various information necessary for operations of the ultrasound observation apparatus 3.

Figure 2:
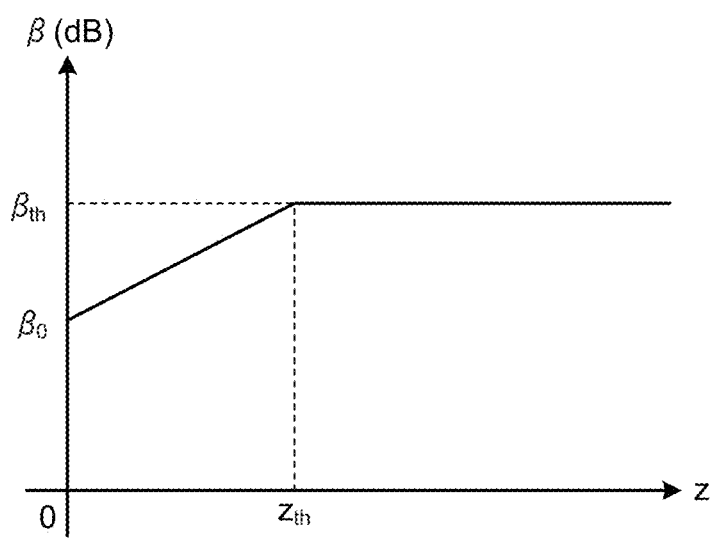
FIG. 2 is a diagram illustrating a relationship between a reception depth and an amplification factor in an amplification process performed by a signal amplification unit of the ultrasound observation apparatus according to the first embodiment of the disclosure.

The transmission/reception unit 31 is configured to include a signal amplification unit 311 for amplifying the echo signal. The signal amplification unit 311 performs sensitivity time control (STC) correction that amplifies the echo signal having a larger reception depth with a higher amplification factor. FIG. 2 is a diagram illustrating the relationship between the reception depth and the amplification factor in the amplification process performed by the signal amplification unit 311. The reception depth z illustrated in FIG. 2 is a quantity calculated on the basis of the elapsed time from the reception start time point of the ultrasound. As illustrated in FIG. 2, when the reception depth z is smaller than the threshold value $z_{th}$, the amplification factor $\beta$ (dB) is linearly increased from $\beta_0$ to $\beta_{th}$ ($>\beta_0$) as the reception depth z is increased. In addition, when the reception depth z is equal to or larger than the threshold value $z_{th}$, a constant value $\beta_{th}$ is taken as the amplification factor $\beta$ (dB). The threshold value $z_{th}$ is such a value that the ultrasound signal received from the observation target is almost attenuated and the noise becomes dominant. More generally, when the reception depth z is smaller than the threshold value $z_{th}$, the amplification factor $\beta$ may be monotonically increased as the reception depth z is increased. In addition, the relationship illustrated in FIG. 2 is stored in advance in the storage unit 37.

The transmission/reception unit 31 performs processing such as filtering on the echo signal amplified by the signal amplification unit 311, performs A/D conversion to generate RF data in the time domain, and outputs the RF data to the signal processing unit 32 and the arithmetic unit 33. In addition, in a case where the ultrasound endoscope 2 has a configuration of allowing the ultrasound transducers 21 having a plurality of elements arranged in an array form to electronically scan, the transmission/reception unit 31 includes a multi-channel circuit for combining beams corresponding to the plurality of elements.

The frequency band of the pulse signal transmitted by the transmission/reception unit 31 is preferably set to a wide band which substantially covers the linear response frequency band of the electro-acoustic conversion of the pulse signal into the ultrasound pulse by the ultrasound transducer 21. In addition, the various processing frequency bands of the echo signal in the signal amplification unit 311 are preferably set to a wide band which substantially covers the linear response frequency band of the acoustic-electric conversion of the ultrasound echo into the echo signal by the ultrasound transducer 21. By these components, it is possible to carry out the approximation with high precision when executing an approximation process for the frequency spectrum to be described later.

The transmission/reception unit 31 has functions of transmitting various control signals outputted by the control unit 36 to the ultrasound endoscope 2 and receiving various types of information including ID for identification from the ultrasound endoscope 2 to transmit to the control unit 36.

The signal processing unit 32 performs known processing such as band pass filtering, envelope detection, and logarithmic conversion on the RF data to generate digital B-mode reception data. In logarithmic conversion, the common logarithm of the amount obtained by dividing RF data by reference voltage $V_c$ is taken and expressed in decibel value. The signal processing unit 32 outputs the generated B-mode reception data to the image processing unit 34. The signal processing unit 32 is realized by using a central processing unit (CPU), various arithmetic circuits, and the like.

The arithmetic unit 33 is configured include an amplification correction unit 331 that performs amplification correction so that the amplification factor $\beta$ (dB) is constant regardless of the reception depth z with respect to the RF data generated by the transmission/reception unit 31, a frequency analysis unit 332 for performing frequency analysis by applying a fast Fourier transform (FFT) to the RF data which is amplified and corrected to calculate a frequency spectrum, a feature calculation unit 333 for calculating the feature of the frequency spectrum on the basis of the frequency spectrum calculated by the frequency analysis unit 332, a display specification setting unit 334 for setting the display specification of the feature to be displayed on the basis of the feature different from the feature of the display target to be displayed on the display device 4. The arithmetic unit 33 is realized by using a CPU, various operation circuits, and the like.

Figure 3:
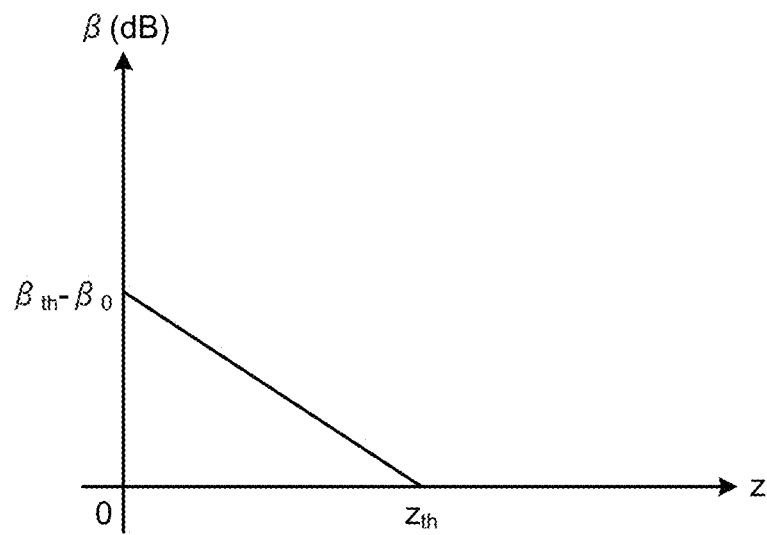
FIG. 3 is a diagram illustrating a relationship between a reception depth and an amplification factor in an amplification correction process performed by an amplification correction unit of the ultrasound observation apparatus according to the first embodiment of the disclosure.

FIG. 3 is a diagram illustrating a relationship between a reception depth and an amplification factor in the amplification correction process performed by the amplification correction unit 331. As illustrated in FIG. 3, the amplification factor $\beta$ in the amplification correction process performed by the amplification correction unit 331 has a maximum value $\beta_{th}-\beta_0$ when the reception depth z is zero, the amplification factor is linearly decreased until the reception depth z reaches the threshold value $z_{th}$ from zero, and the amplification factor is zero when the reception depth z is equal to or larger than the threshold value $z_{th}$. The amplification correction unit 331 amplifies and corrects the digital RF signal according to the amplification factor $\beta$ determined in this manner, so that it is possible to offset the influence of the STC correction in the signal processing unit 32 and output a signal with a constant amplification factor $\beta_{th}$. The relationship between the reception depth z and the amplification factor $\beta$ performed by the amplification correction unit 331 varies according to the relationship between the reception depth and the amplification factor in the signal processing unit 32.

The reason for performing such amplification correction will be described. The STC correction is a correction process for eliminating the influence of attenuation from the amplitude of the analog signal waveform by amplifying the amplitude of the analog signal waveform uniformly over the entire frequency band and with an amplification factor monotonically increasing with respect to the depth. For this reason, in the case of generating a B-mode image in which the amplitude of the echo signal is converted into luminance to display and in the case of scanning a uniform tissue, the luminance value is constant regardless of the depth by performing the STC correction. Namely, it is possible to obtain the effect of eliminating the influence of attenuation from the luminance value of the B-mode image.

On the other hand, as in the embodiment, in the case of using the result of calculating and analyzing the frequency spectrum of the ultrasound, it is not possible to precisely eliminate the influence of the attenuation accompanying the propagation of the ultrasound even by the STC correction. This is because, in general, the attenuation varies depending on the frequency (refer to the Equation (1) described later), but the amplification factor of the STC correction varies depending only on the distance, and there is no frequency dependency.

In order to solve the above-mentioned problem, namely, the problem that, in the case of using the result of calculating and analyzing the frequency spectrum of ultrasound, it is not possible to precisely eliminate the influence of attenuation accompanying the propagation of ultrasound even with STC correction, it is considered to output a reception signal subjected to the STC correction at the time of generating a B-mode image and to perform new transmission different from the transmission for generating the B-mode image and output a reception signal that has not been subjected to the STC correction at the time of generating an image based on the frequency spectrum. However, in this case, there is a problem that the frame rate of the image data generated on the basis of the reception signal is lowered.

Therefore, in the embodiment, in order to eliminate the influence of the STC correction on the signal subjected to the STC correction for the B-mode image while maintaining the frame rate of the generated image data, the amplification correction unit 331 performs the correction of the amplification factor.

The frequency analysis unit 332 samples the RF data (line data) of each sound ray amplified and corrected by the amplification correction unit 331 at predetermined time intervals to generate sample data. The frequency analysis unit 332 calculates a frequency spectrum at a plurality of positions (data positions) on the RF data by applying an FFT process to the sample data group. The term "frequency spectrum" as used herein denotes "frequency distribution of intensity at a certain reception depth z" obtained by applying the FFT process on a sample data group. In addition, the term "intensity" as used herein denotes, for example, a parameter such as a voltage of an echo signal, a power of an echo signal, a sound pressure of an ultrasound echo, or acoustic energy of an ultrasound echo, amplitude or time integral value of the parameters, or a combination thereof.

In general, in a case where the observation target is a living tissue, the frequency spectrum tends to vary depending on the characterization of the living tissue scanned with ultrasound. This is because the frequency spectrum has a correlation with the size, number density, acoustic impedance, or the like of the scatterer which scatters the ultrasound. "The characterization of the living tissue" referred to herein denotes, for example, malignant tumor (cancer), benign tumor, endocrine tumor, mucous tumor, normal tissue, cyst, vascular, and the like.

Figure 4:
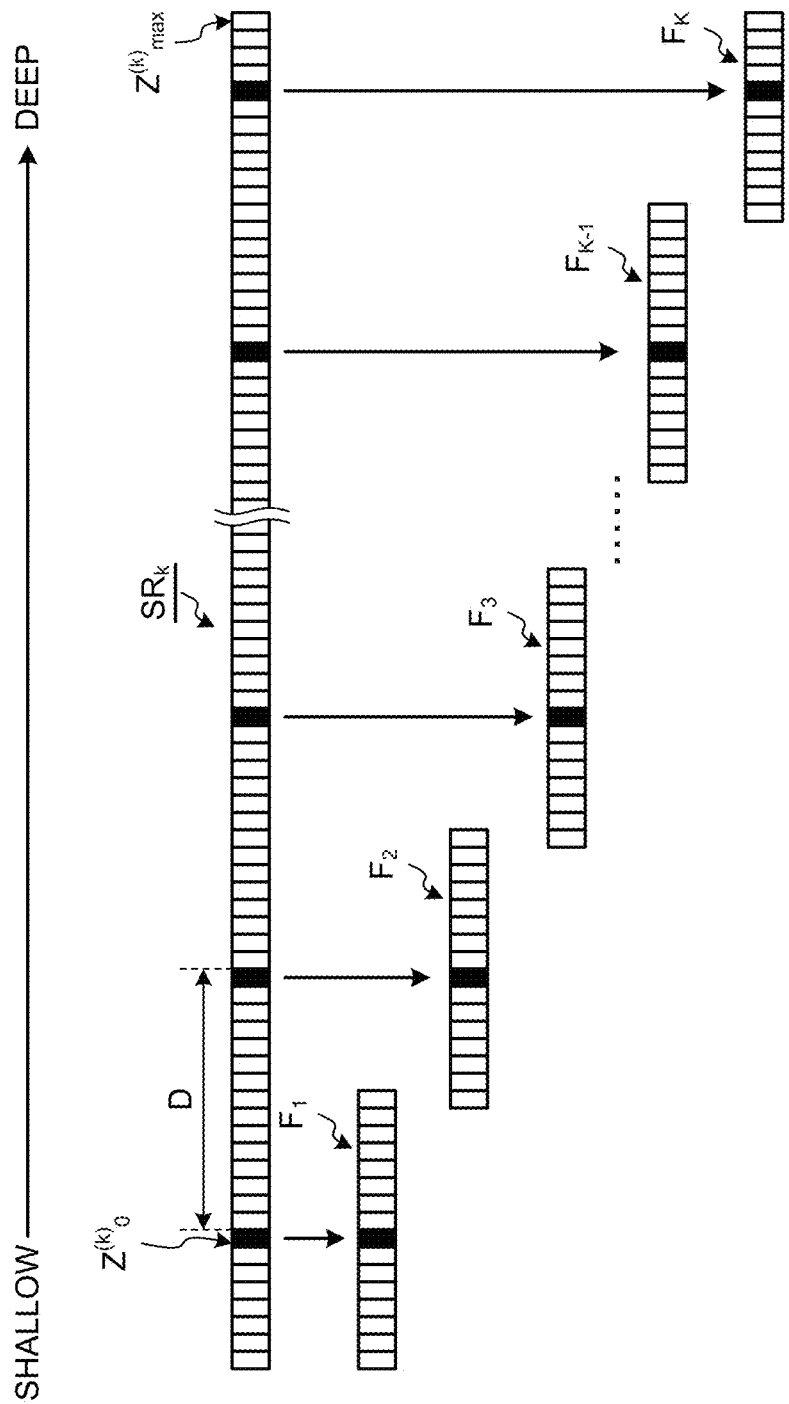
FIG. 4 is a diagram schematically illustrating a data arrangement in one sound ray of an ultrasound signal.

FIG. 4 is a diagram schematically illustrating a data arrangement in one sound ray of an ultrasound signal. In the sound ray $SR_k$ illustrated in the figure, a white or black rectangle denotes data at one sample point. In addition, in the sound ray $SR_k$, the data located on the right side is sample data from a deep portion measured from the ultrasound transducer 21 along the sound ray $SR_k$ (refer to the arrow in FIG. 4). The sound ray $SR_k$ is discretized at a time interval corresponding to the sampling frequency (for example, 50 MHz) in the A/D conversion performed by the transmission/reception unit 31. FIG. 4 illustrates a case where the eighth data position of the sound ray $SR_k$ with the number k is set as the initial value $Z^{(k)}_0$ in the direction of the reception depth z, but the position of the initial value may be arbitrarily set. The calculation result by the frequency analysis unit 332 is obtained as a complex number and stored in the storage unit 37.

The data group $F_j$ (j=1, 2, . . . , K) illustrated in FIG. 4 is a sample data group to be subjected to the FFT process. In general, in order to perform the FFT process, it is necessary for the sample data group to have data number of power of 2. In this sense, the sample data group $F_j$ (j=1, 2, . . . , K−1) is a normal data group having the number of data being 16 (=$2^4$). On the other hand, the sample data group $F_K$ has the number of data being 12, and thus, the sample data group $F_K$ is an abnormal data group. When the FFT process is to be performed on an abnormal data group, a process for generating a normal sample data group by inserting zero data corresponding to the shortage is performed. This point will be described in detail in the process of the frequency analysis unit 332 (refer to FIG. 9).

Figure 5:
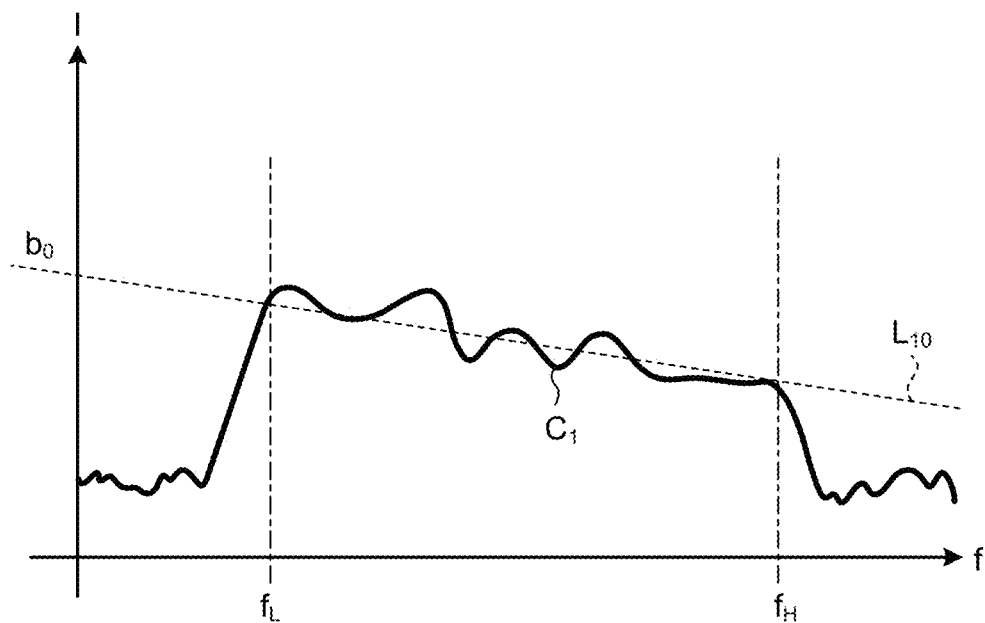
FIG. 5 is a diagram illustrating an example of a frequency spectrum calculated by a frequency analysis unit of the ultrasound observation apparatus according to the first embodiment of the disclosure.

FIG. 5 is a diagram illustrating an example of the frequency spectrum calculated by the frequency analysis unit 332. In FIG. 5, the horizontal axis represents the frequency f. In addition, in FIG. 5, the vertical axis represents a common logarithm (decibel expression) I=10 $\log_{10}$ ($I_0/I_c$) of an amount obtained by dividing an intensity $I_0$ by a reference intensity $I_c$ (constant). A straight line $L_{10}$ illustrated in FIG. 5 will be described later. In the embodiment, curves and straight lines are configured with discrete sets of points.

In the frequency spectrum $C_1$ illustrated in FIG. 5, a lower limit frequency $f_L$ and an upper limit frequency $f_H$ of the frequency band used for the subsequent arithmetic operation are parameters determined on the basis of the frequency band of the ultrasound transducer 21, the frequency band of the pulse signal transmitted by the transmission/reception unit 31, or the like. Hereinafter, in FIG. 5, the frequency band determined by the lower limit frequency $f_L$ and the upper limit frequency $f_H$ is referred to as a "frequency band F".

The feature calculation unit 333 calculates features of a plurality of frequency spectra in the set region of interest (ROI). The feature calculation unit 333 is configured include an approximation unit 333a that calculates a feature of a frequency spectrum (hereinafter, referred to as a pre-correction feature) before performing an attenuation correction process by approximating the frequency spectrum with a straight line and an attenuation correction unit 333b that calculates a feature by performing an attenuation correction process on the pre-correction feature calculated by the approximation unit 333a.

The approximation unit 333a performs a regression analysis of the frequency spectrum in a predetermined frequency band and approximates the frequency spectrum with a linear equation (regression line) to calculate the pre-correction feature featuring the approximated linear equation. For example, in the case of the frequency spectrum $C_1$ illustrated in FIG. 5, the approximation unit 333a obtains the regression line $L_{10}$ by performing a regression analysis in the frequency band F and approximating the frequency spectrum $C_1$ by a linear equation. In other words, the approximation unit 333a calculates, as the pre-correction feature, a mid-band fit $c_0=a_0 f_M+b_0$ which is a value on the regression line $L_{10}$ having slope $a_0$ of the regression line, intercept $b_0$, and center frequency $f_M=(f_L+f_H)/2$ of the frequency band F.

Among the three pre-correction features, the slope $a_0$ has a correlation with the size of the scatterer of the ultrasound, and it is generally considered that the larger the scatterer, the smaller the slope. The intercept $b_0$ has a correlation with the size of the scatterer, a difference in acoustic impedance, the number density (concentration) of the scatterers, and the like. Specifically, it is considered that the intercept $b_0$ has a larger value as the size of the scatterer is larger, has a larger value as the difference in acoustic impedance is larger, and has a larger value as the number density of the scatterers is larger. The mid-band fit $c_0$ is an indirect parameter derived from the slope $a_0$ and the intercept $b_0$ and gives the intensity of the spectrum at the center within the effective frequency band. For this reason, it is considered that the mid-band fit $c_0$ has a certain degree of correlation with luminance of the B-mode image in addition to the size of the scatterer, a difference in acoustic impedance, and the number density of the scatterers. In addition, the feature calculation unit 333 may approximate the frequency spectrum with a polynomial of second or higher order by regression analysis.

The correction performed by the attenuation correction unit 333b will be described. In general, the attenuation amount A (f, z) of the ultrasound is an attenuation occurring while the ultrasound reciprocates between the reception depth 0 and the reception depth z, the attenuation amount is defined as a change in intensity before and after the reciprocation (a difference in decibel expression). It is empirically known that the attenuation amount A (f, z) is proportional to the frequency in a uniform tissue and is expressed by the following Equation (1).

$$A(f,z) = 2\alpha z f \quad (1)$$

Herein, the proportional constant α is an amount called an attenuation factor. In addition, z is the reception depth of the ultrasound, and f is the frequency. A specific value of the attenuation factor α is determined depending on a portion of a living body when the observation target is the living body. The unit of the attenuation factor α is, for example, dB/cm/MHz. In addition, in the embodiment, it is possible to change the value of the attenuation factor α by the input from the input unit 35.

The attenuation correction unit 333b performs the attenuation correction on the pre-correction features (slope $a_0$, intercept $b_0$, and mid-band fit $c_0$) extracted by the approximation unit 333a according to the following equations (2) to (4) to calculate features "a", "b", and "c".

$$a = a_0 + 2\alpha z \quad (2)$$

$$b = b_0 \quad (3)$$

$$c = c_0 + A(f_m, z) = c_0 + 2\alpha z f_M (= a f_M + b) \quad (4)$$

As apparent from the equations (2) and (4), the attenuation correction unit 333b performs the correction with a larger correction amount as the reception depth z of ultrasound is larger. In addition, according to the Equation (3), the correction on the intercept is the identity transformation. This is because the intercept is a frequency component corresponding to frequency 0 (Hz) and is not influenced by the attenuation.

Figure 6:
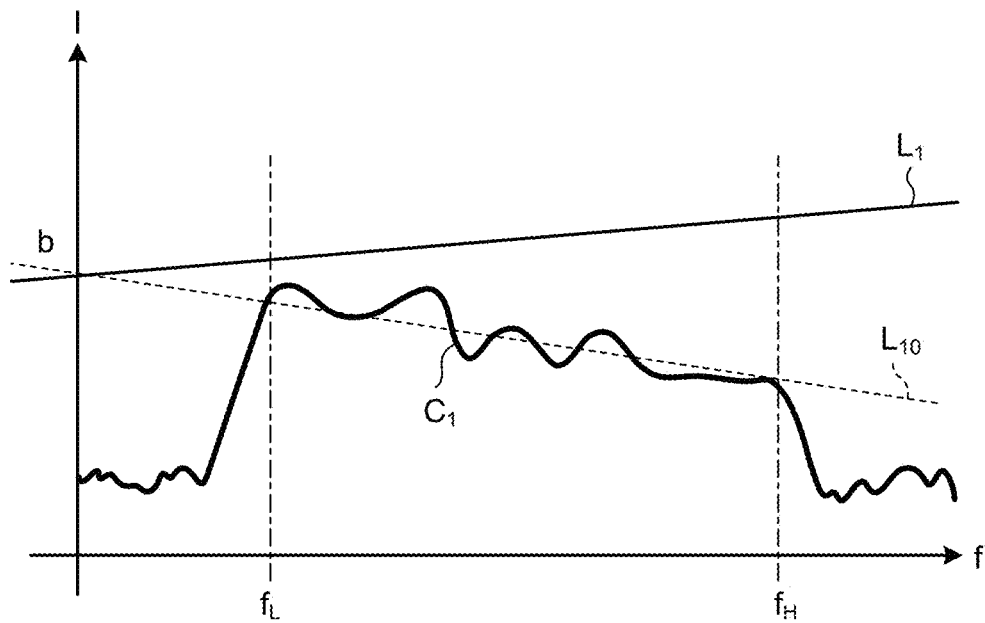
FIG. 6 is a diagram illustrating a straight line having a corrected feature corrected by an attenuation correction unit of the ultrasound observation apparatus according to the first embodiment of the disclosure as a parameter.

FIG. 6 is a diagram illustrating a straight line having the features "a", "b", and "c" calculated by the attenuation correction unit 333b as parameters. The equation of the straight line $L_1$ is expressed as follows.

$$l = af + b = (a_0 + 2\alpha z)f + b_0 \quad (5)$$

As apparent from the Equation (5), the straight line $L_1$ has a larger slope ($a > a_0$) and the same intercept ($b = b_0$) in comparison with the straight line $L_{10}$ before the attenuation correction.

Figure 7:
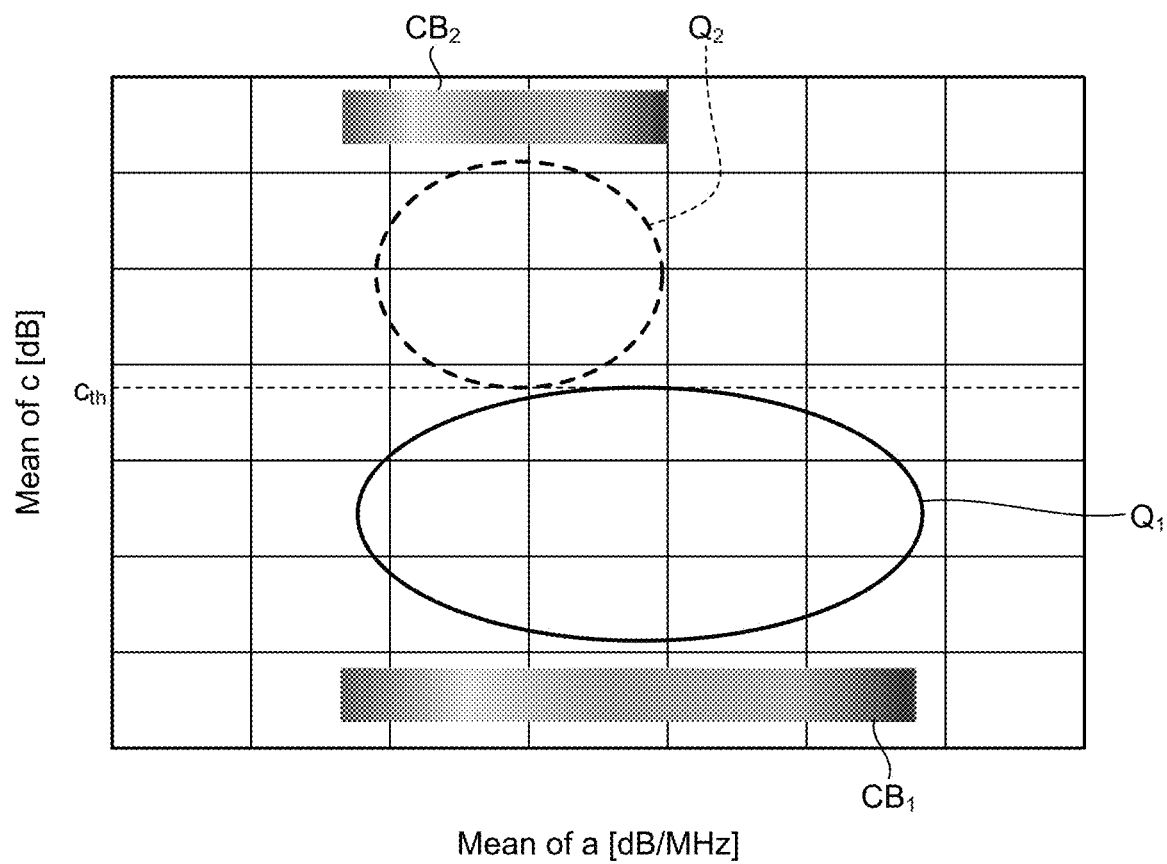
FIG. 7 is a diagram illustrating a process executed by a display specification setting unit of the ultrasound observation apparatus according to the first embodiment of the disclosure.

The display specification setting unit 334 sets the display specification of the feature to be displayed on the basis of the features different from the features of the display target to be displayed on the display device 4. Specifically, in the first embodiment, the display specification setting unit 334 sets the hue scale, which is the display specification of the feature "a" indicating the slope, on the basis of the feature "c" indicating the mid-band fits. The hue scale referred to in this description denotes that colors (hues) having different light wavelengths are arranged in a continuous manner (including multiple steps) and the hues and the values of the features are associated with each other. In FIG. 7, the closer to the left, the closer to red; and the closer to the right, the closer to blue. Specifically, from the left, red, orange, yellow, green, and blue are arranged in the descending order of the wavelength of visible light. For example, the shortest wavelength is 380 nm and the longest wavelength is 750 nm. FIG. 7 is a diagram illustrating a process executed by the display specification setting unit 334 of the ultrasound observation apparatus 3 according to the first embodiment of the disclosure. In FIG. 7, the horizontal axis represents the feature "a". In addition, in FIG. 7, the vertical axis represents the feature "c". FIG. 7 is a graph illustrating a distribution of the feature "a" and the feature "c".

As illustrated in FIG. 7, the distribution of the feature "a" and the feature "c" differs depending on the type of the characterization of the living tissue (hereinafter, referred to as a tissue characterization). For example, certain tissue characterization is distributed in region $Q_1$, and other tissue characterization is distributed in region $Q_2$. In this case, when the feature "a" is expressed with the same hue scale, although one tissue characterization is clearly expressed according to the value of the feature "a", the difference in the value of the feature "a" is not clearly expressed in the other tissue characterization, or the value of the feature "a" is distributed in an region deviated from the hue scale and the feature "a" is not displayed.

In the first embodiment, the display specification setting unit 334 sets the display specification of the feature "a" of a display target on the basis of the feature "c". Specifically, the display specification setting unit 334 obtains the average value of the plurality of features "c" calculated by the feature calculation unit 333, for example, the average value of the features in the set region of interest, compares the average value with a threshold value $c_{th}$, and sets the hue scale on the basis of the comparison result. For example, when the average value of the feature "c" is smaller than the threshold value $c_{th}$, the display specification setting unit 334 sets the hue scale to a hue scale $CB_1$. On the other hand, when the average value of the feature "c" is equal to or larger than the threshold value $c_{th}$, the display specification setting unit 334 sets the hue scale to a hue scale $CB_2$ having a different colorization range from the hue scale $CB_1$. In this manner, by setting the hue scale of the feature "a" on the basis of the feature "c", it is possible to set the hue scale corresponding to the tissue characterization according to a distribution of the feature "a" and the feature "c".

The image processing unit 34 is configured to include a B-mode image data generation unit 341 for generating B-mode image data which is an ultrasound image to be displayed by converting the amplitude of the echo signal into the luminance and a feature image data generation unit 342 for generating feature image data in which the feature calculated by the attenuation correction unit 333b is displayed together with the B-mode image in association with visual information.

The B-mode image data generation unit 341 generates the B-mode image data by performing signal processing by using known techniques such as gain processing and contrast processing on the B-mode reception data received from the signal processing unit 32 and by performing data thinning according to the data step width determined according to the display range of the image in the display device 4. The B-mode image is a grayscale image in which the values of R (red), G (green), and B (blue) which are variables when adopting a RGB color system as a color space are matched.

The B-mode image data generation unit 341 performs coordinate transformation for rearranging the B-mode reception data from the signal processing unit 32 so that the scanning range can be spatially correctly expressed and, after that, performs interpolation between the B-mode reception data to fill gaps between the B-mode reception data and generate the B-mode image data. The B-mode image data generation unit 341 outputs the generated B-mode image data to the feature image data generation unit 342.

The feature image data generation unit 342 generates feature image data by superimposing visual information relating to the features calculated by the feature calculation unit 333 on each pixel of the image in the B-mode image data. The feature image data generation unit 342 allocates, for example, to a pixel region corresponding to the data amount of one sample data group $F_j$ (j=1, 2 . . . , K) illustrated in FIG. 4, visual information corresponding to the feature of the frequency spectrum calculated from the sample data group $F_j$. For example, the feature image data generation unit 342 generates feature image data by associating the hue as the visual information with any one of the above-described slope, intercept, and mid-band fit. Specifically, in the case of associating the hue as the visual information with the feature "a", the feature image data generation unit 342 allocates the visual information by referring to the hue scale set by the display specification setting unit 334. As the visual information relating to the feature, in addition to the hue, for example, there may be exemplified variables of a color space constituting a predetermined color system such as saturation, brightness, luminance value, R (red), G (green), and B (blue).

The control unit 36 is realized by using a CPU (Central Processing Unit) having arithmetic and control functions, various arithmetic circuits, and the like. The control unit 36 reads the information stored and retained by the storage unit 37 from the storage unit 37 and executes various arithmetic processes relating to a method of operating the ultrasound observation apparatus 3, so as to control overall of the ultrasound observation apparatus 3. It is also possible to configure the control unit 36 by using the CPU and the like common to the signal processing unit 32 and the arithmetic unit 33.

The storage unit 37 stores the plurality of features calculated for each frequency spectrum by the attenuation correction unit 333b and the image data generated by the image processing unit 34. In addition, the storage unit 37 is configured to include a display specification information storage unit 371 that stores a distribution of two features out of the plurality of features as illustrated in FIG. 7, a threshold value for performing allocating and setting the hue scale in the distribution, and the plurality of hue scales for each combination of the features.

In addition to the above, the storage unit 37 stores, for example, information necessary for the amplification process (relationship between the amplification factor and the reception depth illustrated in FIG. 2), information necessary for the amplification correction process (relationship between the amplification factor and the reception depth illustrated in FIG. 3), information necessary for the attenuation correction process (refer to the Equation (1)), Information relating to window function (Hamming, Hanning, Blackman, or the like) necessary for the frequency analysis process, and the like.

In addition, the storage unit 37 stores various programs including an operation program for executing the method of operating the ultrasound observation apparatus 3. The operation program may also be recorded on a computer-readable recording medium such as a hard disk, a flash memory, a CD-ROM, a DVD-ROM, or a flexible disk and distributed widely. In addition, the above-described various programs may also be acquired by downloading via a communication network. The communication network referred to herein is realized by, for example, an existing public line network, a local area network (LAN), a wide area network (WAN), and the like and may be wired or wireless.

The storage unit 37 having the above configuration is realized by using a read only memory (ROM) in which various programs and the like are preliminarily installed, a random access memory (RAM) for storing arithmetic parameters and data of each process, and the like.

Figure 8:
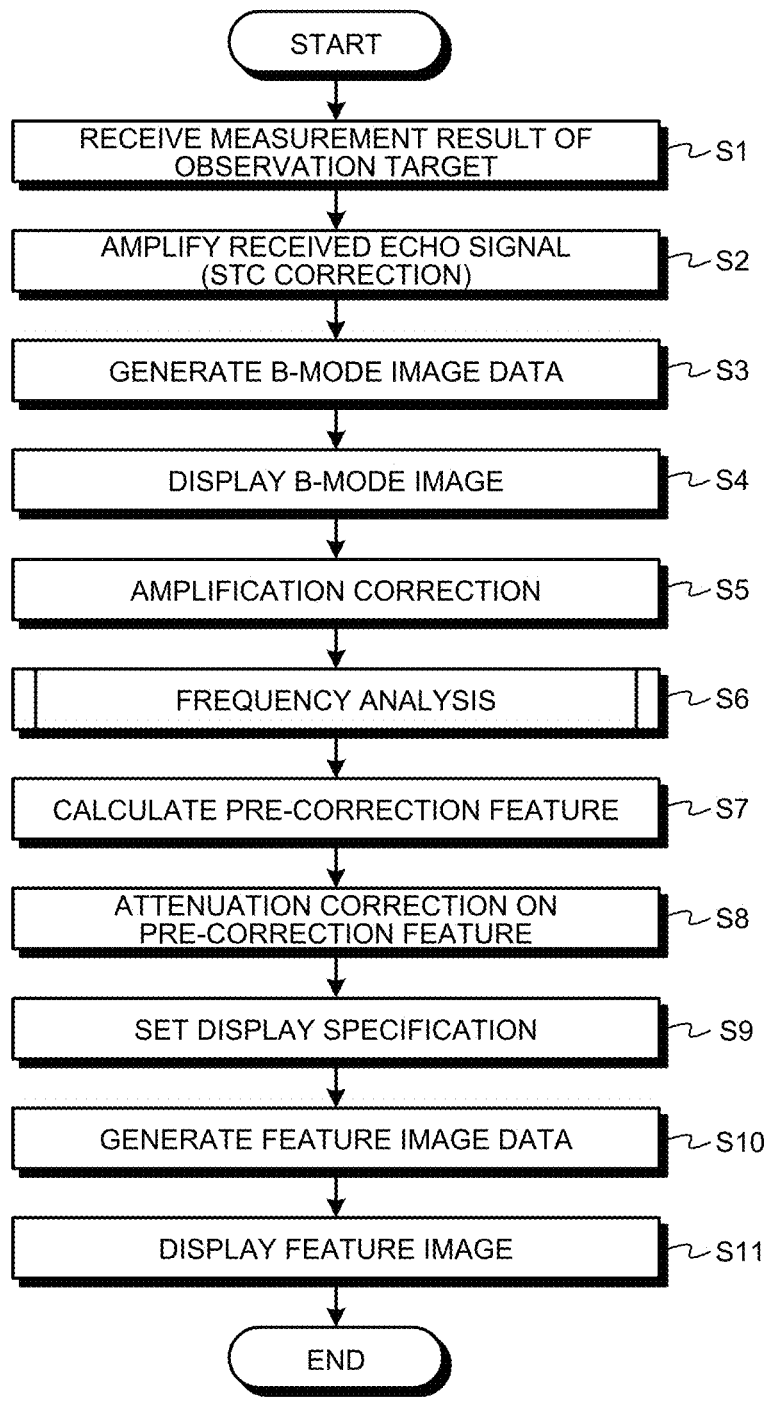
FIG. 8 is a flowchart illustrating an overview of processes performed by the ultrasound observation apparatus according to the first embodiment of the disclosure.

FIG. 8 is a flowchart illustrating the overview of the processes performed by the ultrasound observation apparatus 3 having the above configuration. First, the ultrasound observation apparatus 3 receives an echo signal as a measurement result of an observation target by the ultrasound transducer 21 from the ultrasound endoscope 2 (Step S1).

Upon receiving the echo signal from the ultrasound transducer 21, the signal amplification unit 311 amplifies the echo signal (Step S2). Herein, for example, the signal amplification unit 311 performs amplification (STC correction) of the echo signal on the basis of the relationship between the amplification factor and the reception depth illustrated in FIG. 2.

Subsequently, the B-mode image data generation unit 341 generates the B-mode image data by using the echo signal amplified by the signal amplification unit 311 and outputs the B-mode image data to the display device 4 (Step S3). Upon receiving the B-mode image data, the display device 4 displays the B-mode image corresponding to the B-mode image data (Step S4).

The amplification correction unit 331 performs amplification correction on the signal output from the transmission/reception unit 31 so that the amplification factor is constant regardless of the reception depth (Step S5). Herein, for example, the amplification correction unit 331 performs amplification correction such that the relationship between the amplification factor and the reception depth illustrated in FIG. 3 is established.

Figure 9:
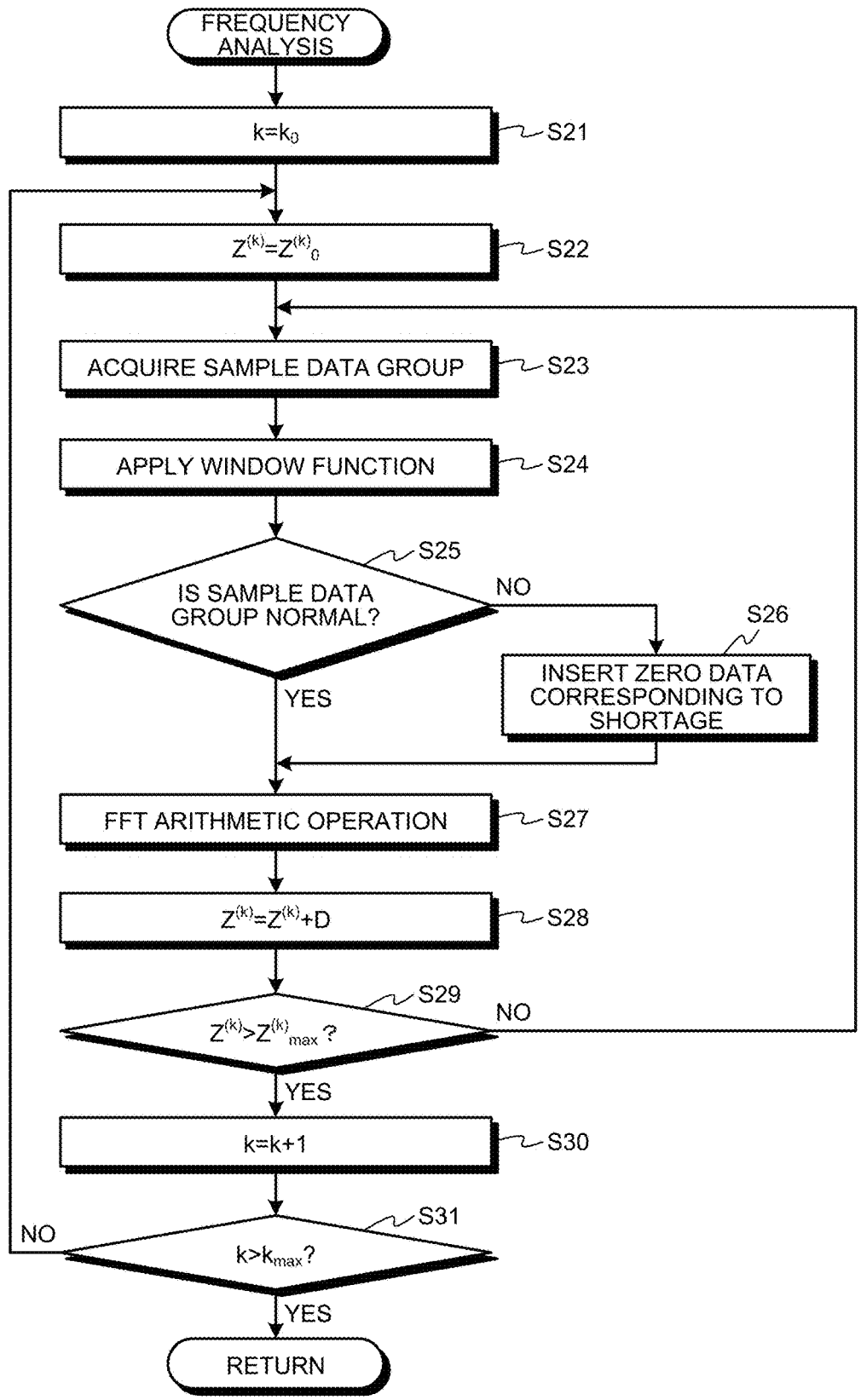
FIG. 9 is a flowchart illustrating an overview of processes executed by a frequency analysis unit of the ultrasound observation apparatus according to the first embodiment of the disclosure.

After that, the frequency analysis unit 332 calculates frequency spectra for all the sample data groups by performing the frequency analysis by the FFT process (Step S6: frequency analysis step). FIG. 9 is a flowchart illustrating the overview of the processing executed by the frequency analysis unit 332 in Step S6. Hereinafter, the frequency analysis process will be described in detail with reference to the flowchart illustrated in FIG. 9.

First, the frequency analysis unit 332 sets the counter k for identifying the sound ray of the analysis target as $k_0$ (Step S21).

Subsequently, the frequency analysis unit 332 sets an initial value $Z^{(k)}_0$ of a data position (corresponding to a reception depth) $Z^{(k)}$ representing a series of the data groups (sample data group) acquired for the FFT process (step S22). For example, FIG. 4 illustrates a case where the eighth data position of the sound ray $SR_k$ is set as the initial value $Z^{(k)}_0$ as described above.

After that, the frequency analysis unit 332 acquires the sample data group (Step S23), and applies the window function stored in the storage unit 37 to the acquired sample data group (Step S24). In this manner, by applying the window function to the sample data group, it is possible to prevent the sample data group from becoming discontinuous at the boundary and to prevent artifacts from occurring.

Subsequently, the frequency analysis unit 332 determines whether or not the sample data group at the data position $Z^{(k)}$ is a normal data group (Step S25). As described with reference to FIG. 4, the sample data group needs to have a data number of a power of 2. Hereinafter, the number of data of the normal sample data group is $2^n$ (n is a positive integer). In the embodiment, the data position $Z^{(k)}$ is set to be the center of the sample data group to which $Z^{(k)}$ belongs as much as possible. Specifically, since the number of data of the sample data group is $2^n$, $Z^{(k)}$ is set to the $2^n/2$ ($=2^{n-1}$)-th position close to the center of the sample data group. In this case, the fact that the sample data group is normal denotes that there are $2^{n-1}-1$ ($=N$) data before the data position $Z^{(k)}$ and there are $2^{n-1}$ ($=M$) data after the data position $Z^{(k)}$. In the case illustrated in FIG. 4, the sample data groups $F_1, F_2, F_3, \ldots$, and $F_{K-1}$ are normal. In addition, in FIG. 4, the case of n=4 (N=7, M=8) is exemplified.

As a result of the determination in Step S25, in a case where the sample data group at the data position $Z^{(k)}$ is normal (Step S25: Yes), the frequency analysis unit 332 proceeds to Step S27 described later.

As a result of the determination in Step S25, in a case where the sample data group at the data position $Z^{(k)}$ is not normal (Step S25: No), the frequency analysis unit 332 generates a normal sample data group by inserting zero data corresponding to the shortage (step S26). In the sample data group (for example, the sample data group $F_K$ in FIG. 4) that is determined not to be normal in Step S25, the window function is applied before adding the zero data. For this reason, no data discontinuity occurs even if the zero data is inserted into the sample data group. After Step S26, the frequency analysis unit 332 proceeds to Step S27 to be described later.

In Step S27, the frequency analysis unit 332 performs the FFT process by using the sample data group to obtain a frequency spectrum which is the frequency distribution of amplitude (Step S27).

Subsequently, the frequency analysis unit 332 changes the data position $Z^{(k)}$ by the step width D (Step S28). It is assumed that the storage unit 37 previously stores the step width D. In FIG. 4, the case of D=15 is exemplified. It is desirable that the step width D is allowed to coincide with the data step width used by the B-mode image data generation unit 341 at the time of generating the B-mode image data. However, in a case where it is desired to reduce the arithmetic amount in the frequency analysis unit 332, a value larger than the data step width may be set as the width D.

After that, the frequency analysis unit 332 determines whether or not the data position $Z^{(k)}$ is larger than the maximum value $Z^{(k)}{}_{max}$ on the sound ray $SR_k$ (Step S29). In a case where the data position $Z^{(k)}$ is larger than the maximum value $Z^{(k)}{}_{max}$ (Step S29: Yes), the frequency analysis unit 332 increments the counter k by 1 (Step S30). This denotes that the process is shifted to an adjacent sound ray. On the other hand, in a case where the data position $Z^{(k)}$ is equal to or smaller than the maximum value $Z^{(k)}{}_{max}$ (Step S29: No), the frequency analysis unit 332 returns to Step S23. In this manner, the frequency analysis unit 332 performs the FFT process on $[(Z^{(k)}{}_{max}-Z^{(k)}{}_0+1)/D+1]$ sample data groups on the sound ray $SR_k$. Herein, [X] represents the largest integer not exceeding X.

After Step S30, the frequency analysis unit 332 determines whether or not the counter k is larger than the maximum value $k_{max}$, (Step S31). In a case where the counter k is larger than the maximum value $k_{max}$ (Step S31: Yes), the frequency analysis unit 332 ends a series of the frequency analysis processes. On the other hand, in a case where the counter k is equal to or smaller than the maximum value $k_{max}$ (Step S31: No), the frequency analysis unit 332 returns to Step S22. The maximum value $k_{max}$ is set to a value arbitrarily entered by the user such as a doctor through the input unit 35 or set in advance in the storage unit 37.

In this manner, the frequency analysis unit 332 performs the FFT process multiple times for each of ($k_{max}-k_0+1$) sound rays within the analysis target region. The result of the FFT process is stored in the storage unit 37 together with the reception depth and the reception direction.

In addition, in the above description, the frequency analysis process is performed on all the regions in which the frequency analysis unit 332 has received the ultrasound signal. However, the frequency analysis process may also be performed only within the set region of interest.

Following the frequency analysis process in Step S6 described above, the feature calculation unit 333 calculates the respective pre-correction features of the plurality of frequency spectra and performs the attenuation correction for eliminating the influence of the attenuation of ultrasound on the pre-correction feature of each frequency spectrum to calculate the corrected feature of each frequency spectrum (Steps S7 to S8: feature calculation step).

In Step S7, the approximation unit 333a performs the regression analysis on each of the frequency spectra generated by the frequency analysis unit 332 to calculate the pre-correction feature corresponding to each frequency spectrum (Step S7). Specifically, the approximation unit 333a approximates each frequency spectrum with a linear equation by performing the regression analysis and calculates the slope $a_0$, the intercept $b_0$, and the mid-band fit $c_0$ as pre-correction features. For example, the straight line $L_{10}$ illustrated in FIG. 5 is a regression line approximated by the approximation unit 333a to the frequency spectrum $C_1$ of the frequency band F by performing the regression analysis.

Subsequently, the attenuation correction unit 333b calculates the corrected feature by performing the attenuation correction on the pre-correction feature approximated to each frequency spectrum by the approximation unit 333a by using the attenuation factor α and stores the calculated corrected feature in the storage unit 37 (Step S8). The straight line $L_1$ illustrated in FIG. 6 is an example of a straight line obtained by the attenuation correction unit 333b performing the attenuation correction process.

In Step S8, the attenuation correction unit 333b calculates the corrected feature by inserting the data position $Z=(f_{sp}/2v_s)$ Dn obtained by using the data array of the sound rays of ultrasound signal at the reception depth z in the equations (2) and (4). Herein, $f_{sp}$ is the data sampling frequency, $v_s$ is the sound velocity, D is the data step width, and n is the number of data steps from the first data of the sound ray to the data position of the sample data group to be processed. For example, if the data sampling frequency $f_{sp}$ is assumed to be 50 MHz, the sound velocity $v_s$ is assumed to be 1530 m/sec, and the data arrangement illustrated in FIG. 4 is adopted so that the step width D is 15, z=0.2295 n (mm).

After that, for each pixel in the B-mode image data generated by the B-mode image data generation unit 341, on the basis of a feature different from the feature to be displayed, among the features calculated in Step S8, the display specification (hue scale) of the feature of the display target is set (Step S9: display specification setting step). For example, a hue scale that is a display specification of the feature "a" indicating the slope is set on the basis of the feature "c" indicating the mid-band fit.

For each pixel in the B-mode image data generated by the B-mode image data generation unit 341, the feature image data generation unit 342 generates feature image data by superimposing the visual information (for example, hue) which is visual information associated with the feature calculated in Step S8 by using the hue scale that has been set in Step S9 (Step S10: feature image data generation step).

Figure 10:
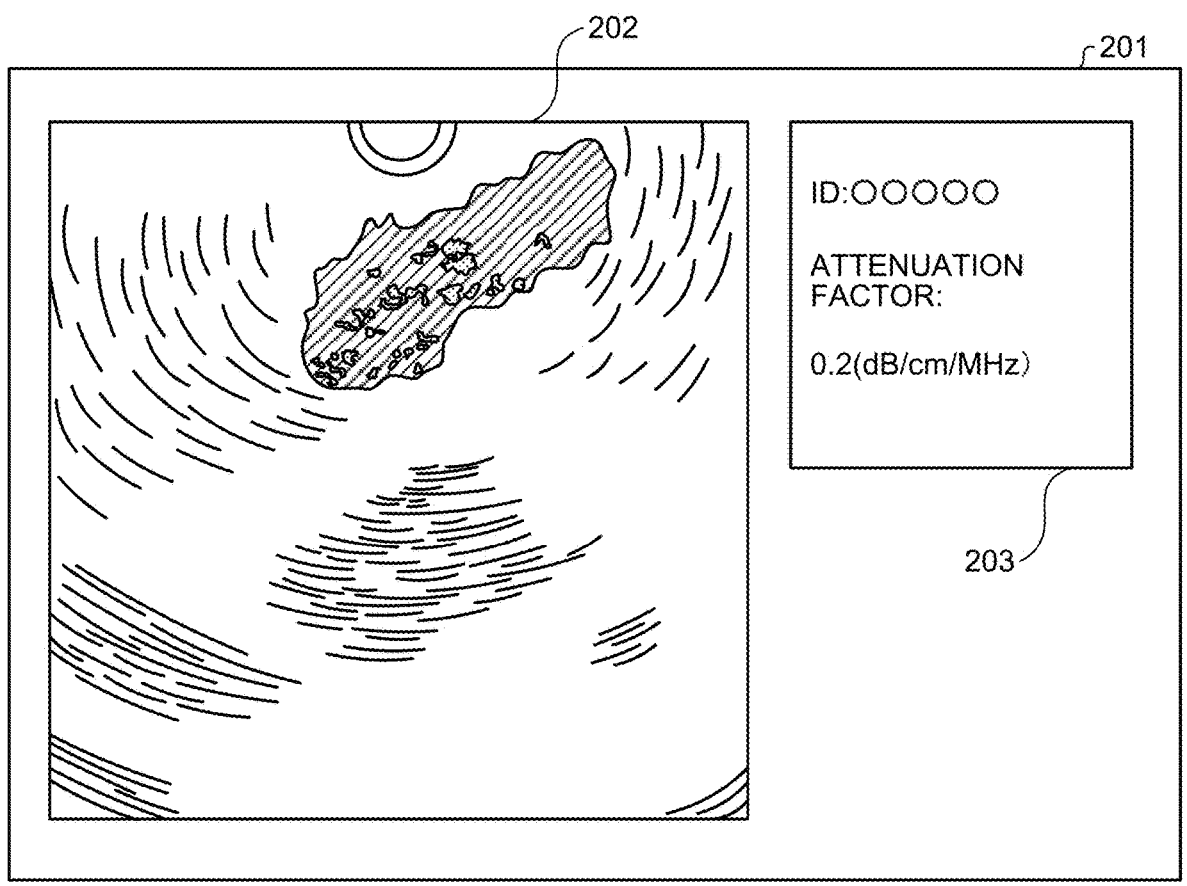
FIG. 10 is a diagram schematically illustrating a display example of feature images in a display device of the ultrasound observation apparatus according to the first embodiment of the disclosure.

After that, under the control of the control unit 36, the display device 4 displays a feature image corresponding to the feature image data generated by the feature image data generation unit 342 (Step S11). FIG. 10 is a diagram schematically illustrating a display example of a feature image on the display device 4. A feature image 201 illustrated in the figure has a superimposed image display portion 202 for displaying an image in which visual information on a feature is superimposed on a B-mode image and an information display portion 203 for displaying identification information or the like of the observation target. In addition, the information display portion 203 may further display information of feature, information of approximate equation, image information such as gain and contrast, and the like. In addition, the B-mode image corresponding to the feature image may be displayed side by side with the feature image.

In the above-described series of processes (Steps S1 to S11), the process of Step S2 and the processes of Steps S4 to S11 may be performed in parallel.

According to the first embodiment of the disclosure described above, the display specification setting unit 334 is configured to set the display specification of the feature "a" of the display target on the basis of the feature "c" different from the feature "a" of the display target to be displayed on the display device 4, so that it is possible to clearly express the difference of the feature by selecting the optimal hue scale from the distribution of the two features.

In addition, in the first embodiment, although it has been described that the display specification setting unit 334 sets the display specification of the feature of the display target on the basis of the average value of the feature different from the feature of the display target to be displayed on the display device 4, the disclosure is not limited thereto, and the hue scale may be set on the basis of a mode value or a median value.

In addition, in the above-described first embodiment, for example, in a case where it is difficult to perform determination by using only one threshold value due to such as region overlapping between tissue characterization in the distribution of the feature "a" and the feature "c", a selection range of the hue scale to be set is set in advance for each region, and the display specification setting unit 334 may set the display specification of the feature of the display target by determining which selection range includes the average value of the feature different from the feature of the display target to be displayed on the display device 4.

Modified Example 1 of First Embodiment

Figure 11:
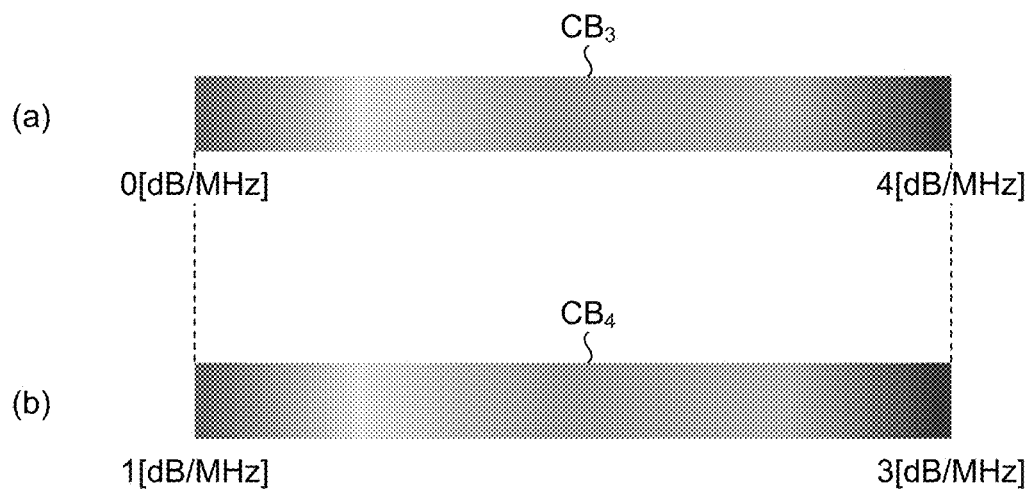
FIG. 11 is a diagram illustrating a process executed by a display specification setting unit of an ultrasound observation apparatus according to modified example 1 of the first embodiment of the disclosure.

FIG. 11 is a diagram illustrating a process executed by the display specification setting unit 334 of the ultrasound observation apparatus 3 according to modified example 1 of the first embodiment of the disclosure. In the above-described first embodiment, it has been described that one-end sides of the hue scales are aligned, for example, that the minimum value of the feature "a" is set to zero [dB/MHz] (refer to FIG. 7). However, the values at both ends of the respective hue scales may be different. For example, the display specification setting unit 334 may set the hue scale $CB_3$ of which range (colorization range) of the value of the feature "a" is 0 to 4 [dB/MHz] as illustrated in (a) of FIG. 11 and the hue scale $CB_4$ of which range of the value of the feature "a" is 1 to 3 [dB/MHz] as illustrated in (b) of FIG. 11 so as to be set in accordance with the value of the feature "c". At this time, the display specification setting unit 334 compares the representative value (for example, the average value or the mode value) of the feature "c" with the threshold value and sets the colorization range on the basis of the comparison result.

Modified Example 2 of First Embodiment

Figure 12:
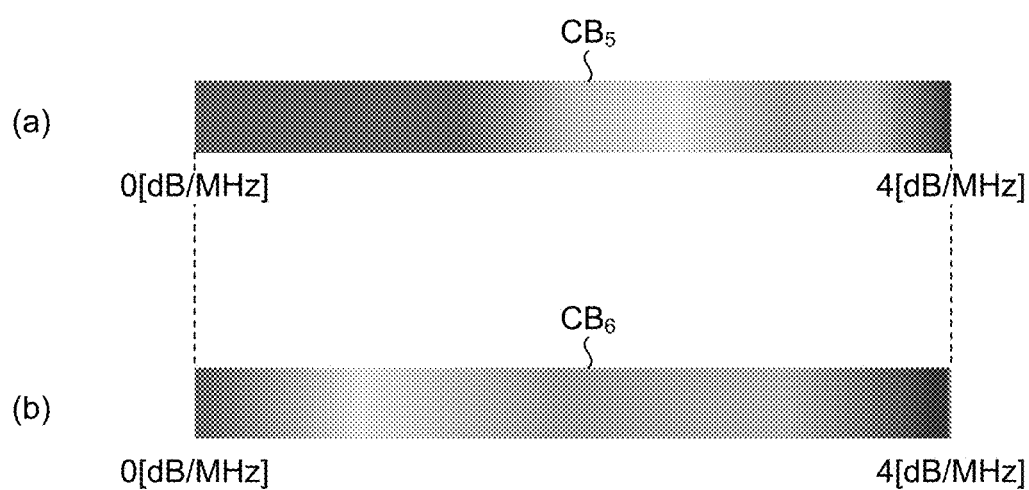
FIG. 12 is a diagram illustrating a process executed by a display specification setting unit of an ultrasound observation apparatus according to modified example 2 of the first embodiment of the disclosure.

FIG. 12 is a diagram illustrating a process executed by the display specification setting unit 334 of the ultrasound observation apparatus 3 according to modified example 2 of the first embodiment of the disclosure. In the above-described first embodiment, it has been described that the hue scales having different colorization ranges of the value of the feature "a" and having the same proportion of the change rate of the hue (refer to FIG. 7) are used. However, the hue scales may have different change rates of the hue. For example, as illustrated in (a) of FIG. 12 and (b) of FIG. 12, the display specification setting unit 334 may set the hue scale $CB_5$ and the hue scale $CB_6$ having the same range of the value of the feature "a" being 0 to 4 dB/MHz and having different change rate of the gradation of the hue in accordance with the value of the feature "c". At this time, the display specification setting unit 334 compares the representative value (for example, the average value or the mode value) of the feature "c" with the threshold value and sets the change rate of the hue on the basis of the comparison result.

Modified Example 3 of First Embodiment

Figure 13:
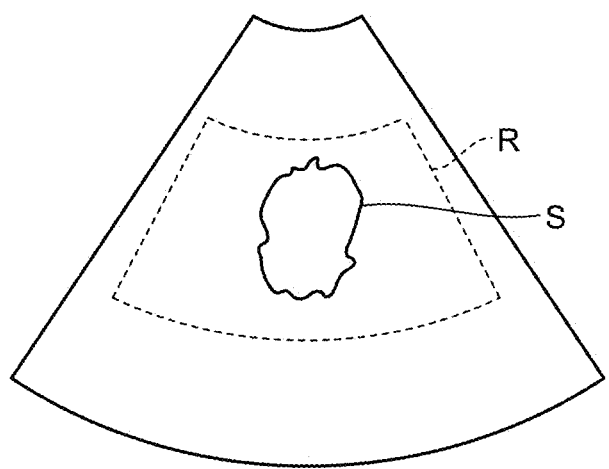
FIG. 13 is a diagram illustrating a process executed by a display specification setting unit of an ultrasound observation apparatus according to modified example 3 of the first embodiment of the disclosure.

FIG. 13 is a diagram illustrating a process executed by the display specification setting unit 334 of the ultrasound observation apparatus 3 according to modified example 3 of the first embodiment of the disclosure. In the above-described first embodiment, it has been described that the display specification setting unit 334 sets the hue scale according to the value of the feature "c" in the region of interest. However, the hue scale may be set according to the value of the feature "c" of the target site in the region of interest. For example, the display specification setting unit 334 sets the hue scale according to the value of the feature "c" on the target site S such as a tumor in the region of interest R as illustrated in FIG. 13. In modified example 3, for example, the hue scale is set according to the value of the feature "c" at the position within the target site S selected by the user through the input unit 35. As a result, the hue scale is allowed to be set on the basis of the feature corresponding to the visual information, so that it is possible to perform more highly accurate display of the feature of the display target.

In addition to the value of the feature in the region of interest, the value of the feature at the position in the target site selected by the user through the input unit 35, the value of the feature of the entire B-mode image may be used.

Second Embodiment

Figure 14:
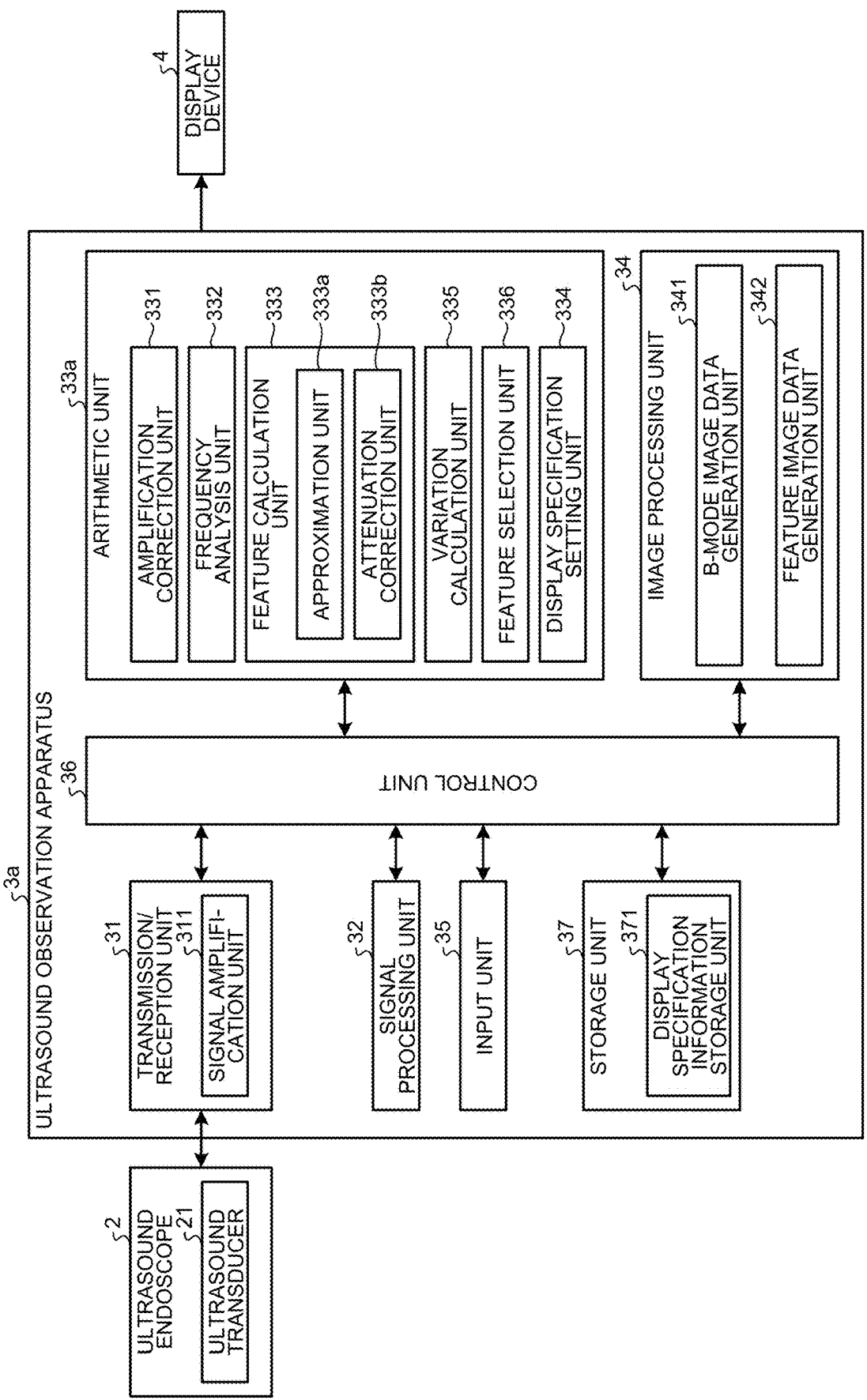
FIG. 14 is a block diagram illustrating a configuration of an ultrasound observation system including an ultrasound observation apparatus according to a second embodiment of the disclosure.

FIG. 14 is a block diagram illustrating a configuration of an ultrasound observation system 1a including an ultrasound observation apparatus 3a according to a second embodiment of the disclosure. The ultrasound observation system 1a illustrated in the figure is configured include the ultrasound observation apparatus 3a instead of the ultrasound observation apparatus 3 of the ultrasound observation system 1 according to the above-described first embodiment. In above-described first embodiment, it has been described that the display specification setting unit 334 sets the hue scale of the feature which is set in advance. However, in the second embodiment, the feature is selected, and the hue scale is set according to a variation of the feature.

An arithmetic unit 33a of the ultrasound observation apparatus 3a is configured include a variation calculation unit 335 and a feature selection unit 336 in addition to the configuration of the arithmetic unit 33 described above. The variation calculation unit 335 calculates variations in the plurality of corrected features calculated by the feature calculation unit 333. Specifically, in a case where the features used for setting the hue scale are the feature "a" and the feature "c", the variation calculation unit 335 obtains variations in the feature "a" and the feature "c", respectively. As the variation, there may be exemplified a variance, a difference between the maximum value and the minimum value of the feature, and the like.

The feature selection unit 336 selects features as a display target by comparing the variations of the two features for which variations have been obtained. Specifically, in a case where the features used for setting the hue scale are the feature "a" and the feature "c", the feature selection unit 336 compares the variation of the feature "a" with that of the feature "c" and selects the feature having a larger variation as the feature of the display target. For example, in a case where the variation of the feature "c" is larger than the variation of the feature "a", the feature selection unit 336 sets the feature "c" as the feature of the display target and sets the hue scale on the basis of the feature "a". In addition, although it has been described that the feature having the larger variation is selected as a display target, the feature having the smaller variation may be selected, and it is preferable to select a feature that can be clearly displayed.

The display specification setting unit 334 sets the display scale of the feature selected by the feature selection unit 336 on the basis of the feature with a large variation.

According to the second embodiment of the disclosure described above, the feature selection unit 336 selects the feature of the display target on the basis of the variation calculated by the variation calculation unit 335, and the display specification setting unit 334 selects the display specification of the feature of the display target on the basis of the feature different from the selected feature (the feature of the display target), so that it is possible to select the feature more clearly expressing the difference and display the feature on the display device 4.

Third Embodiment

Figure 15:
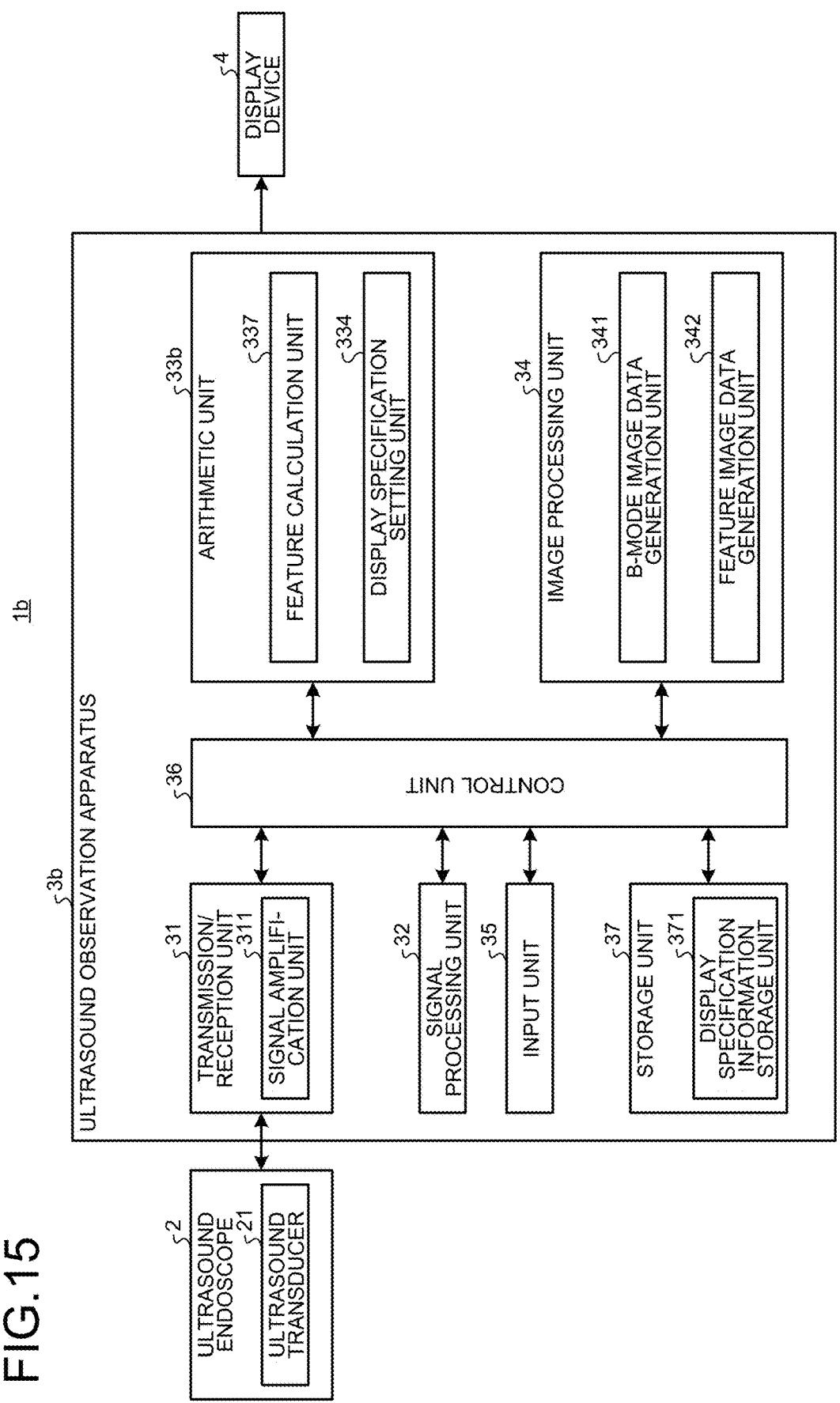
FIG. 15 is a block diagram illustrating a configuration of an ultrasound observation system including an ultrasound observation apparatus according to a third embodiment of the disclosure.

FIG. 15 is a block diagram illustrating a configuration of an ultrasound observation system 1b including an ultrasound observation apparatus 3b according to a third embodiment of the disclosure. The ultrasound observation system 1b illustrated in the figure is configured to include an ultrasound observation apparatus 3b instead of the ultrasound observation apparatus 3 of the ultrasound observation system 1 according to the above-described first embodiment. In the above-described first embodiment, it has been described that the display specification setting unit 334 sets the hue scale according to the values of the features "a" and "c" calculated on the basis of the frequency spectrum. However, in the third embodiment, the hue scale indicating the sound velocity is set according to the value of the hardness.

An arithmetic unit 33b in the ultrasound observation apparatus 3b is configured to include a feature calculation unit 337 instead of the amplification correction unit 331, the frequency analysis unit 332, and the feature calculation unit 333 of the arithmetic unit 33 described above. The feature calculation unit 337 calculates the sound velocity and the hardness at each position on the basis of the RF data generated by the transmission/reception unit 31. The feature calculation unit 337 obtains the sound velocity by calculating the time until the ultrasound transmitted from the ultrasound transducer 21 is reflected by the observation target and returns on the basis of the RF data. In addition, the feature calculation unit 337 obtains the hardness by calculating the amount of change per unit time on the basis of the plurality of RF data at each position.

Figure 16:
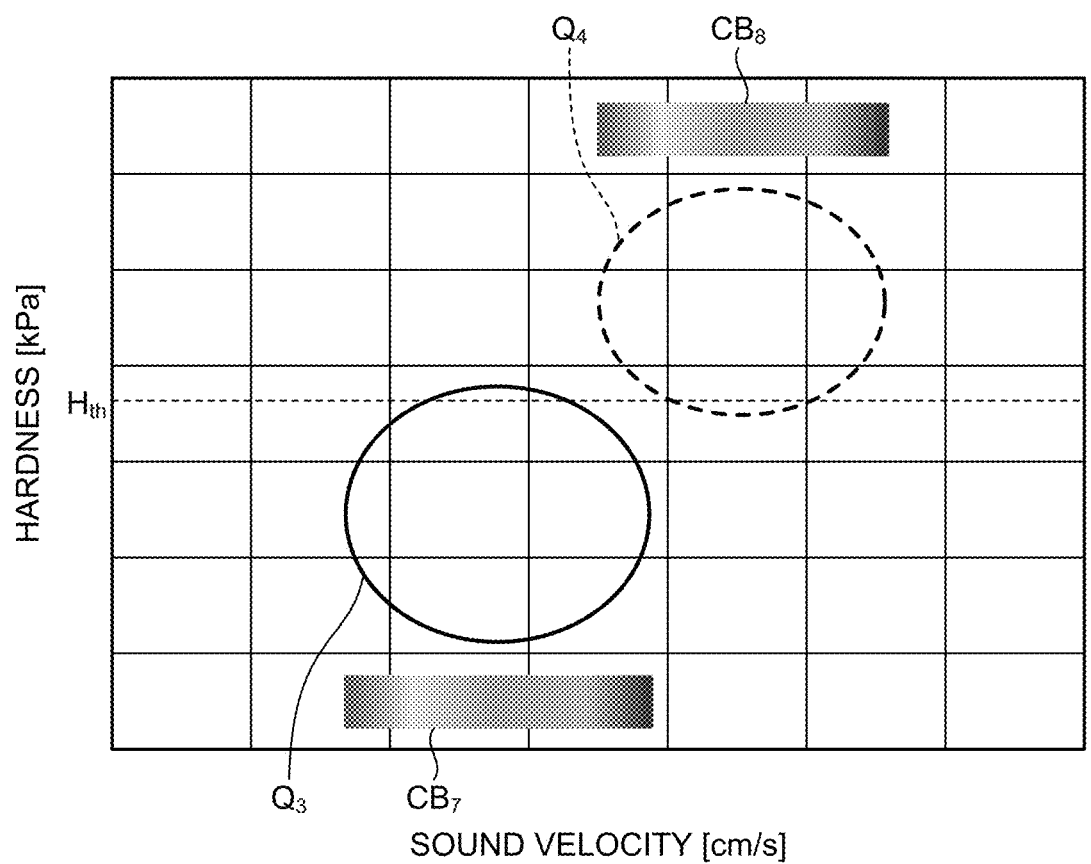
FIG. 16 is a diagram illustrating a process executed by a display specification setting unit of the ultrasound observation apparatus according to the third embodiment of the disclosure.

The display specification setting unit 334 according to the third embodiment sets the hue scale which is the display specification of the sound velocity as the feature on the basis of the hardness which is a feature different from the hue scale. FIG. 16 is a diagram illustrating a process executed by the display specification setting unit 334 of the ultrasound observation apparatus 3b according to the third embodiment of the disclosure. In FIG. 16, the horizontal axis represents the sound velocity (cm/s). In addition, in FIG. 16, the vertical axis represents the hardness (kPa). FIG. 16 is a graph illustrating the distribution of sound velocity and hardness.

Herein, as illustrated in FIG. 16, the distribution of sound velocity and hardness differs depending on the type of the characterization of the living tissue (hereinafter, referred to as tissue characterization). For example, a certain tissue characterization is distributed in region $Q_3$, and other tissue characterization is distributed in region $Q_4$. At this time, if the sound velocity is expressed with the same hue scale, one tissue characterization is clearly expressed according to the value of the sound velocity, but the difference in the value of the sound velocity may not be clearly expressed in the other tissue characterization. In addition, the value of the sound velocity is distributed in a region deviated from the hue scale, and thus, the sound velocity may not be displayed.

In the third embodiment, the display specification setting unit 334 sets the display specification of the sound velocity of the display target on the basis of the hardness. Specifically, the display specification setting unit 334 obtains an average value of the plurality of hardnesses calculated by the feature calculation unit 337, compares the average value with a threshold value $H_{th}$, and sets the hue scale on the basis of the comparison result. For example, in a case where the average value of the hardness is smaller than the threshold value $H_{th}$, the display specification setting unit 334 sets the hue scale $CB_7$ according to the range of the sound velocity in the region $Q_3$ by referring to the display specification information storage unit 371. On the other hand, in a case where the average value of the hardness is equal to or larger than the threshold value $H_{th}$, the display specification setting unit 334 sets the hue scale $CB_8$ according to the range of the sound velocity in the region $Q_4$ by referring to the display specification information storage unit 371. In this manner, by setting the hue scale of the sound velocity on the basis of the hardness, it is possible to set the hue scale corresponding to the tissue characterization according to the distribution of sound velocity and hardness.

According to the third embodiment of the disclosure described above, the display specification setting unit 334 sets the display specification of the feature (hardness) of the display target on the basis of the feature (hardness) different from the feature (sound velocity) of the display target to be displayed on the display device 4, so that it is possible to clearly express the difference of the feature by selecting the optimum hue scale from the distribution of the two features.

Heretofore, although the modes for carrying out the disclosure have been described, the disclosure is not be limited only by the embodiments described above. In the first to third embodiments described above, it has been described that the hue scale of one feature of the two features is set on the basis of another feature of the two features, but the disclosure is not limited thereto. For example, three features may be used, each feature may be represented by the three orthogonal axes in a coordinate system, and the hue scale of the feature of the display target may be set on the basis of the other two features among the three features. In this case, the threshold value is spatially set by the other two features. In addition, the frequency feature, the sound velocity and the hardness may be set, or the attenuation amount may be used as the feature. In the embodiment, the hue scale is set by using at least two features of the features "a", "b", and "c", which are frequency features, the sound velocity, the hardness, and the attenuation amount.

In addition, the first to third embodiments described above, two hue scales are set according to a distribution of tissue characterization, but the disclosure is not limited thereto. If there are three or more distributions (regions) corresponding to tissue characterization, the hue scales that can be set are also stored in the display specification information storage unit 371 according to the number of the hue scales. In addition, if the change rates of the hues are the same on the plurality of hue scales of the setting target and the central values (average value, median value, mode value) of each region of the plurality of tissue characterization are on a straight line, the colorization range may be set by sliding according to the threshold value.

In addition, in the first to third embodiments described above, the hue scale is set according to a certain threshold value, but it is also possible to set the range of the feature according to the distribution of the tissue characterization and to set the hue scale by determine in which range the value of the feature different from the display target may be included.

As described above, the disclosure may include various embodiments within the scope without deviating from the technical idea described in the claims.

As described above, an ultrasound observation apparatus, an operation method of an ultrasound observation apparatus, and an operation program for an ultrasound observation apparatus according to the disclosure are useful for clearly expressing a difference in feature.

According to some embodiments, it is possible to clearly express a difference in feature.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound observation apparatus for generating an ultrasound image based on an ultrasound signal acquired by an ultrasound probe, the ultrasound probe including an ultrasound transducer configured to transmit ultrasound to an observation target and receive the ultrasound reflected from the observation target, comprising:
   a feature calculation unit configured to calculate a plurality of features based on the ultrasound signal;
   a feature image data generation unit configured to generate feature image data in which a feature of a display target to be displayed together with the ultrasound image, among the plurality of features calculated by the feature calculation unit, are colorized with a predetermined display specification; and
   a display specification setting unit configured to set at least one of a colorization range of the feature of the display target and a change rate of hue of the feature of the display target, which are display specifications of the feature of the display target, by comparing a representative value of other feature other than the feature of the display target with a threshold value.

2. The ultrasound observation apparatus according to claim 1,
   wherein the display specification setting unit is configured to set the display specification of the feature of the display target, based on a feature of a target region in an image based on the ultrasound signal which is the other feature.

3. The ultrasound observation apparatus according to claim 1, further comprising a frequency analysis unit configured to analyze a frequency of a signal generated based on the ultrasound signal to calculate a plurality of frequency spectra,
   wherein the feature calculation unit is configured to calculate a frequency feature based on a frequency spectrum calculated by the frequency analysis unit as one of the plurality of features.

4. The ultrasound observation apparatus according to claim 3,
   wherein the feature of the display target is any one of a sound velocity, a hardness, an attenuation amount, and the frequency feature, and
   wherein the other feature is at least one feature different from the feature of the display target, among the sound velocity, the hardness, the attenuation amount, and the frequency feature.

5. The ultrasound observation apparatus according to claim 3,
   wherein the feature calculation unit is configured to linearly approximate the frequency spectrum calculated by the frequency analysis unit to calculate the frequency feature.

6. The ultrasound observation apparatus according to claim 5,
   wherein the frequency feature is at least one of a slope, an intercept and a mid-band fit obtained by approximating the frequency spectrum calculated by the frequency analysis unit.

7. The ultrasound observation apparatus according to claim 1, further comprising:
   a variation calculation unit configured to calculate a variation of each of the features; and
   a feature selection unit configured to select a feature of the display target based on the variation of each of the features calculated by the variation calculation unit,
   wherein the display specification setting unit is configured to set a display specification of the feature of the display target based on other feature other than the feature of the display target selected by the feature selection unit.

8. A method of operating an ultrasound observation apparatus for generating an ultrasound image based on an ultrasound signal acquired by an ultrasound probe, the ultrasound including an ultrasound transducer configured to transmit ultrasound to an observation target and receive the ultrasound reflected from the observation target, the method comprising:
   calculating, by a feature calculation unit, a plurality of features based on the ultrasound signal;

setting, by comparing a representative value of other feature other than a feature of a display target to be displayed together with the ultrasound image, among the plurality of features calculated by the feature calculation unit, with a threshold value by a display specification setting unit, at least one of a colorization range of the feature of the display target and a change rate of hue of the feature of the display target, which are display specifications of the feature of the display target; and generating, by a feature image data generation unit, feature image data in which the feature of the display target is colorized with a predetermined display specification.

9. A non-transitory computer-readable recording medium with an executable program stored thereon, the program causing an ultrasound observation apparatus for generating an ultrasound image based on an ultrasound signal acquired by an ultrasound probe, the ultrasound including an ultrasound transducer configured to transmit ultrasound to an observation target and receive the ultrasound reflected from the observation target, to execute:

calculating, by a feature calculation unit, a plurality of features based on the ultrasound signal;

setting, by comparing a representative value of other feature other than a feature of a display target to be displayed together with the ultrasound image, among the plurality of features calculated by the feature calculation unit, with a threshold value by a display specification setting unit, at least one of a colorization range of the feature of the display target and a change rate of hue of the feature of the display target, which are display specifications of the feature of the display target; and generating, by a feature image data generation unit, feature image data in which the feature of the display target is colorized with a predetermined display specification.

* * * * *